United States Patent [19]

Delany

[11] Patent Number: 4,999,368
[45] Date of Patent: Mar. 12, 1991

[54] SELECTIVE PYRAZOLINE INSECTICIDES AND FUNGICIDES, COMPOSITIONS AND USE

[75] Inventor: John J. Delany, Rochester, N.Y.

[73] Assignee: Eastman Kodak Company, Rochester, N.Y.

[21] Appl. No.: 478,881

[22] Filed: Feb. 12, 1990

[51] Int. Cl.$^5$ .................... A61K 43/56; C07D 231/08
[52] U.S. Cl. ................................ 514/403; 514/232.2; 514/236.5; 544/82; 544/140; 548/379
[58] Field of Search ................ 544/82, 140; 548/379; 514/232.2, 236.5, 403

[56] References Cited

U.S. PATENT DOCUMENTS 4,358,525 11/1982 Mooberry et al. ................ 430/217

Primary Examiner—Robert W. Ramsuer
Attorney, Agent, or Firm—Betty J. Deaton

[57] ABSTRACT

A pyrazoline having the formula:

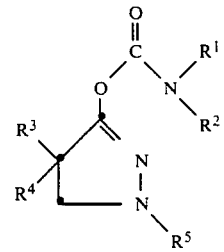

wherein:
  $R^1$ and $R^2$ are selected independently from a group consisting of hydrogen with the proviso that only one of $R^1$ and $R^2$ can be hydrogen, substituted or unsubstituted alkyl of from 1-20 carbon atoms and substituted or unsubstituted aryl of 6 to 20 carbons, or $R^1$ and $R^2$ can together comprise the atoms necessary to complete a heterocyclic group of 5 to 6 nuclear carbon and hetero atoms;
  $R^3$ and $R^4$ are selected independently from a group consisting of hydrogen, substituted or unsubstituted alkyl of from 1-20 carbon atoms, substituted or unsubstituted aryl of 6-20 carbon atoms, alkoxy, alkylthio, cycloalkyl or heterocyclyl of 5 to 6 nuclear carbon and hetero atoms, or $R^3$ and $R^4$ together are an alkylene group of 4 to 5 carbon atoms.

$R^5$ is selected from a group consisting of substituted or unsubstituted alkyl of 1-10 carbon atoms, alkenyl of 1-10 carbon atoms, substituted or unsubstituted aryl of 6-20 carbon atoms and cycloalkyl of 5 to 6 nuclear carbon atoms.

Compounds of the above formula are useful as aphicides and fungicides.

19 Claims, No Drawings

SELECTIVE PYRAZOLINE INSECTICIDES AND FUNGICIDES, COMPOSITIONS AND USE

FIELD OF THE INVENTION

The present invention relates to insecticides and fungicides.

BACKGROUND OF THE INVENTION

In view of world hunger, it is useful to provide the public with a variety of insecticides and fungicides for use in food agriculture.

Of the insecticides known in the art, U.S. Pat. No. 4,537,901 dated Aug. 27, 1985 and entitled "Insecticidal Carbamates", assigned to BASF Aktiengesellschaft, Fed. Rep. of Germany, discloses that carbamates having the following structure have insecticidal properties.

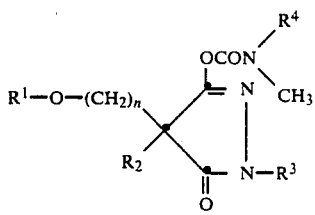

However, these compounds have an oxo group in the 1 position. Similar compounds are disclosed in U.S. Pat. No. 4,213,992 dated July 22, 1980 and entitled "Insecticidal Carbamates", assigned to BASF Aktiengesellschaft, Fed. Rep. of Germany.

In U.S. Pat. No. 3,810,911, entitled "N,N-Dimethyl-0(1-Alkyl-4-Cyano-5-Alkoxy-pyrazol(3)yl)-Carbamic acid Esters, dated May 14, 1974, assigned to Bayer Aktiengesellachaft, Leverkusen, Germany, carbamic acid esters of the following structure are disclosed:

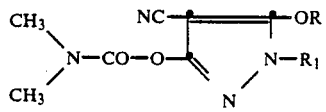

Acaricidal and insecticidal properties are disclosed. However, this compound has two double bonds within the heterocyclic ring as opposed to one. Also, it has a cyano group at the $R^3$-$R^4$ position according to the generic formula of this invention.

Similar compounds are disclosed in U.S. Pat. No. 3,996,367 entitled "N,N-Dimethyl-0-[1-Methyl-3-N-Methylcarbaminyl-Methyl-Pyrazol(5)YL]Carbamic Acid Ester" dated Dec. 7, 1976 assigned to Bayer Aktiengesellschaft, Leverkusen, Germany, U.S. Pat. No. 4,535,901, entitled "0-Pyrazolyl-N-Cyanoalkyl Sulphenyl-Carbamate Pesticides" dated Aug. 13, 1985 assigned to Bayer Aktiengesellschaft, Leverkusen, Germany, U.S. Pat. No. 4,423,058 entitled "Combating Pests With Novel Pyrazol-4-yl N-Alkyl Carbamates" dated Dec. 27, 1983 assigned to Bayer Aktiengesellschaft, Leverkusen, Germany.

SUMMARY OF THE INVENTION

The present invention relates to new 1-alkyl or aryl-3-(substituted carbamoyloxy)-2-pyrazolines and their use as pest-combating agents and fungicides.

The novel compound has the formula:

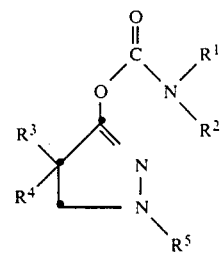

wherein:

$R^1$ and $R^2$ are selected independently from a group consisting of hydrogen with the proviso that only one of $R^1$ and $R^2$ can be hydrogen, substituted or unsubstituted alkyl of from 1-20 carbon atoms and substituted or unsubstituted aryl of 6 to 20 carbons, or $R^1$ and $R^2$ can together comprise the atoms necessary to complete a heterocyclic group of 5 to 6 nuclear carbon and hetero atoms;

$R^3$ and $R^4$ are independently selected from a group consisting of hydrogen, substituted or unsubstituted alkyl of from 1-20 carbon atoms, substituted or unsubstituted aryl of 6-20 carbon atoms, alkoxy, alkylthio, cycloalkyl or hetercyclyl of 5 or 6 nuclear carbon and hetero atoms, or $R^3$ and $R^4$ together are an alkylene group of 4 to 5 carbon atoms.

$R^5$ is selected from a group consisting of substituted or unsubstituted alkyl of 1-10 carbon atoms, alkenyl of 1-10 carbon atoms, substituted or unsubstituted aryl of 6-20 carbon atoms and cycloalkyl of 5 or 6 nuclear carbon atoms.

The compounds are useful in providing an alternative for presently known aphicides and fungicides.

DESCRIPTION OF THE PREFERRED EMBODIMENTS

The novel compounds useful as insecticides have the following formula:

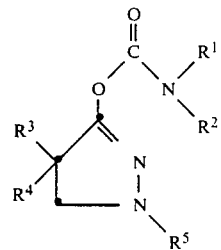

wherein:

$R^1$ and $R^2$ are selected independently from a group consisting of hydrogen with the proviso that only one of $R^1$ and $R^2$ can be hydrogen, substituted or unsubstituted alkyl of from 1-20 carbon atoms including alkyl groups having hetero atoms or hetero- atom-containing groups as substituents (monovalent) or as interrupting groups in the alkyl chain (divalent) such as hydroxy, mercapto, alkoxy such as methoxy, alkylthio such as methylthio, carboxy, ester, i.e., alkylcarbonyloxy, arylcarbonyloxy, alkoxycarbonyl, aryloxycarbonyl, etc., carbamoyl, e.g., N,N-dimethylcarbamoyl, etc., carbamoyloxycarb- onyl such as N,N-dimethylcarbamoyloxycarbonyl, ureido such as N',N'-dimethyl-N-methylsulfonylureido, oxy, oxo, thio, thioxo, sulfamoyl, halo such as chloro, bromo, fluoro, and iodo, etc., and $R^1$ and $R^2$ are additionally selected from substituted or unsubstituted aryl of about 6 to 20 carbon atoms, or $R^1$ and $R^2$ can together comprise the atoms necessary to complete a heterocyclic group of 5 or 6 nuclear carbon and hetero atoms in the heterocyclic ring;

$R^3$ and $R^4$ are selected independently from a group consisting of hydrogen, substituted or unsubstituted alkyl of from 1–20 carbon atoms, substituted or unsubstituted aryl of 6–20 carbon atoms, alkoxy and alkylthio where alkyl and the alkyl portion of said alkoxy and alkylthio groups are as defined for $R^1$ and $R^2$ and cycloalkyl of 5 or 6 nuclear carbon atoms, or $R^3$ and $R^4$ taken together represent an alkylene group of 4 to 5 nuclear carbon atoms, preferably a tetramethylene or pentamethylene group, so that $R^3$, $R^4$ and the carbon to which they are attached form a carbocyclic group having 5 to 6 nuclear carbon atoms.

$R^5$ is selected from a group consisting of substituted or unsubstituted alkyl of about 1–10 carbon atoms, alkenyl of 1–10 carbon atoms, substituted or unsubstituted aryl of 6–20 carbon atoms and cycloalkyl of 5 or 6 nuclear carbon atoms, suitable substituents on said alkyl, alkenyl, and aryl groups including straight or branched alkyl of about 1 to 6 carbon atoms, aryl of about 6 to 12 carbon atoms, halogen, e.g., chloro, bromo, fluoro, and iodo, alkoxy, e.g., methoxy, propoxy, etc., amido, e.g., N,N-dimethylcarbamoyl, sulfonamido, e.g., N,N-dimethylsulfamoyl, and othe known groups which do not destroy the aphicidal properties of the molecule, exemplary $R^5$ groups being o-tolyl, p-tolyl, 4-methoxyphenyl, phenyl, 2-bromophenyl, 4-bromophenyl, 2-fluorophenyl, 3-fluorophenyl, 4-fluorophenyl, 4-chlorophenyl, 3,4-dichlorophenyl, 2,4,6-trichlorophenyl, 4-butylphenyl, 4-(N,N-dimethylcarbamoyloxycarbonylphenyl), 4-(N',N'-dimethyl-N-methylsulfonylureido)phenyl, allyl, benzyl, 2-methoxybenzyl, 4-fluorobenzyl, 4-t-butylbenzyl, methylbenzyl, nitrophenyl, etc.

Particularly preferred compounds of this invention include compounds having the above formula wherein $R^1$, $R^2$, and $R^3$ and $R^4$ are methyl and $R^5$ is selected independently from a group consisting of substituted or unsubstituted alkyl of about 1–10 carbon atoms, substituted or unsubstituted alkenyl of 1–10 carbon atoms, substituted or unsubstituted aryl of 6–20 carbon atoms and cycloalkyl of 5 or 6 nuclear carbon atoms, suitable substituents on said alkyl, alkenyl, and aryl groups including straight or branched alkyl of about 1 to 6 carbon atoms, aryl of about 6 to 12 carbon atoms, halogen, e.g., chloro, bromo, fluoro, and iodo, alkoxy, e.g., methoxy, propoxy, etc., amido, e.g., N,N-dimethylcarbamoyl, sulfonamido, e.g., N,N-dimethylsulfonyl, and other known groups which do not destroy the aphicidal properties of the molecule, exemplary $R^5$ groups being o-tolyl, p-tolyl, 4-methoxyphenyl, phenyl, 2-bromophenyl, 4-bromophenyl, 2-fluorophenyl, 3-fluorophenyl, 4-fluorophenyl, 4-chlorophenyl, 3,4-dichlorophenyl, 2,4,6 trichlorophenyl, 4-butylphenyl, 4-(N,N-dimethylcarbamoyloxycarbonyl)phenyl, 4-(N',N'-dimethyl-N-methylsulfonylureido)phenyl, allyl, benzyl, 2-methoxybenzyl, 4-fluorobenzyl, 4-t-butylbenzyl, methylbenzyl, nitrophenyl, etc.

Depending on the substituents, the new pyrazolidinones are colorless or light yellow oils or colorless crystalline solids exhibiting a strong biological action which permits their use as insecticides. The compounds have an excellent action on sucking insects, especially aphids. They are also active against flies and wheat leaf rust.

The compounds of the invention are useful in providing an alternative to presently known insecticides and fungicides. Particularly, many compounds of this invention have the quality of performing both a fungicidal and insecticidal function. The invention provides active compositions in the form of mixtures of such compounds with solid and liquid dispersible carrier vehicles and methods for producing such compounds in a new way especially for combating aphids, flies and/or wheat rust.

The compounds of the invention are prepared by the condensation of a 1-aryl-3-pyrazolidinone with an N,N-dialkylcarbamoyl chloride. The 1-aryl-3-pyrazolidinone is prepared by using a combination of the Kendall et al and Allen et al references, i.e., U.S. Pat. No. 2,688,024, entitled "Production of 3-Pyrazolidinones" issued on Aug. 31, 1954 to Kendall, et al and assigned to Ilford Ltd. and U.S. Pat. No. 2,772,282 entitled "3-Pyrazolidinones" issued on Nov. 27, 1956 to Allen, et al and assigned to Eastman Kodak Company. The Kendall and Allen references disclose a process for producing 3-pyrazolidinones comprising reacting a hydrazine of the general formula $RNH.NH_2$ where R is a hydrogen atom or a hydrocarbon group, with an ester. The N,N-dialkylcarbamoyl chloride may be purchased from Aldrich Chemical Co.

If, for example, 4,4-Dimethyl-3-(N,N-dimethylcarbamoyloxy-1-phenyl-2-pyrazoline is prepared through the condensation of 4,4-dimethyl-1-phenyl-3-pyrazolidinone with N,N-dimethylcarbamoyl chloride, the reaction which proceeds can be outlined by the following equation:

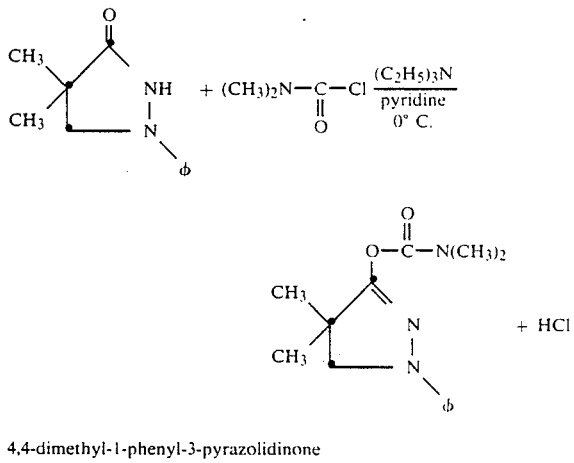

4,4-dimethyl-1-phenyl-3-pyrazolidinone

In carrying out the process, the starting materials are generally employed in equimolar (stoichiometric) amounts. The reaction is promoted by an excess of up to 200% of the carbamyl halide.

The reaction is carried out in a solvent or a diluent inert to the reactants. Pyridine is the preferred solvent. Examples of suitable solvents or diluents are ethers, such as a diethyl ether, diisopropyl ether, tetrahydrofuran, dioxane or diglycol dimethyl ether, aliphatic chlorohydrocarbons, such as dichloromethane, trichloromethane, carbon tetrachloride, 1,1-dichloroethane or 1,2-dichloroethane, aromatic hydrocarbons, such as toluene, xylenes, or chlorobenzenes, dimethylformamide, nitromethane, and nitriles, such as acetonitrile or propionitrile.

Organic bases can be used as acid scavengers in the reaction. Aliphatic, aromatic or heterocyclic amines are preferred bases such as triethylamine, trimethylamine, dimethylaniline, dimethylbenzylamine, pyridine and diazabicycloundecene since organic bases produce organic salts which are highly insoluble in non-polar media.

The reaction temperature can range from 0° degrees Celcius to 100° C. The preferred temperature range is 20°-50° C. The boiling point of the diluent may constitute an upper limit for the temperature.

The reaction mixture is then diluted with a solvent, preferably methylene chloride. Other solvents can be used such as ethyl acetate, diethyl ether, diisopropyl ether or any aliphatic chlorohydrocarbon described above.

Next, the reaction mixture is washed with 10% aqueous hydrochloric acid. Other washing agents could be used such as saturated aqueous ammonium chloride or saturated sodium bicarbonate.

Finally, the organic layer is dried (MgSO$_4$), filtered and evaporated. Other drying agents can be used such as Na$_2$SO$_4$ and K$_2$CO$_3$.

Aqueous formulations may be prepared from emulsion concentrates, pastes, oil dispersions or wettable powders by adding water. To prepare emulsions, pastes and oil dispersions the ingredients as such, or dissolved in an oil or solvent, may be homogenized in water by means of surfactants as wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of lignin-sulfonic acid, naphthalenesulfonic acids, phenolsulfonic acids, alkylarylsulfonates, alkyl sulfates, and alkylsulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulose powders, etc.

The active compounds according to the invention can furthermore be present in commercially available formulations and in the use forms, prepared from these formulations, as a mixture with synergistic agents, Synergistic agents are compounds which increase the action of the active compounds, without it being necessary for the synergist added to be active itself.

The active compound content of the use forms, prepared from the commerically available formulations can vary within wide limits. The active compound concentration of the use forms can be from 0.001 to 95% by weight of active compound, preferably between 0.01 and 90% by weight. Carrier composition mixtures suitable for direct application or field application generally contemplate those in which the active compound is present in an amount substantially between about 0.0001-10%, preferably 0.001-2% by weight of the mixture. Thus, the present invention contemplates overall compositions which comprise mixtures of a conventional dispersible carrier vehicle such as a dispersible carrier liquid such as an inert organic solvent and/or water preferably including a surface-active effective amount of a carrier vehicle assistant, e.g., a surface active agent, such as an emulsifying agent and/or a dispersing agent, and an amount of the active compound which is effective for the purpose in question and which is generally between about 0.0001-95% and preferably 0.001-95% by weight of the mixture.

The active ingredients may also be successfully used in the ultra-low volume method, where it is possible to apply formulations containing up to 95% of active ingredient, or even the 100% active ingredient.

An example of a formulation is given below: 25 g of 1-(2-bromophenyl)-4,4-dimethyl-3-(N,N-dimethylcarbamoyloxy)-2-pyrazoline and 2.5 g octylphenoxy polyethoxy ethanol(triton x-100 surfactant sold by Rohm & Haas) in 2.5 l acetone and water to make up to 25 l.

There may be added to the individual active ingredients or mixtures thereof [if desired, immediately before use (tankmix)] oils of various types, herbicides, fungicides, insecticides and bactericides.

Examples of active ingredients which may be admixed are described in U.S. Pat. No. 4,213,992 entitled "Insecticidal Carbamates" issued on July 22, 1980 to Aldophi et al.

These agents may be added to the compounds according to the invention in a ratio by weight of from 1:10 to 10:1.

The active ingredient according to the invention may be used for combatting pests such as sucking insects, including aphids such as *Myzus persicae, Doralis fabae, Rhopalosiphum padi., Macrosiphum pisi, Macrosiphum solanifolii, Cryptomyzus korschelti, Sapaphis mali, Hyalopterus arundinis* and *Aphis fabae, Aphis pomi, Aphis sambuci, Aphidula nasturii, Coro apha gosypii, Sapaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acrythosiphon onobrychus, Macrosiphon rosae, Megoura viciae, Schizoneura Lanuginosa, Eriosoma lanigerum, Pemphigus bursarius, Dreyfusia nordmannianae, Dreyfusia piceae* and *Adelges laricis*.

It is also useful for combatting flies such as *Drosophila melanogaster, Ceratitis capitata, Musca domestica, Fan-*

*nia cancicularis, Phormia regina, Calliphora erythrocephala* and *Stomoxys calcitrans.*

It is also useful for combatting wheat leaf rust (*Puccinia recondita*).

Application of the active ingredients may be effected for instance in the form of directly sprayable solutions, powders, suspensions, dispersions, emulsions, oil dispersions, pastes, dusts, broadcasting agents, or granules by spraying atomizing, dusting, broadcasting or watering. The forms of application depend entirely on the purpose for which the agents are being used; in any case they should ensure a fine distribution of the active ingredient.

As liquid diluents or carriers, especially solvents, there are suitable in the main, aromatic hydrocarbons, such as xylene, toluene or alkyl naphthalenes, chlorinated aliphatic hydrocarbons, such as chlorobenzenes, chloroethylenes or methylene chloride, aliphatic hydrocarbons, such as cyclohexane or parafins, for examples mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl sulphoxide, as well as water.

By liquified gaseous diluents or carriers are meant liquids which would be gaseous at normal temperatures and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly dispersed silicic acid, alumina and silicates. As solid carriers for granules there may be used crushed and fractionated natural rocks such as calcite, marble, pumice, sepiolite and dolomite, as well as synthetic granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, lignin sulfphite waste liquors and methyl-cellulose.

Adhesives such as carboxymethyl cellulose and natural and synthetic polymers in the form of powders, granules or latices, such as gum arabic, poly(vinyl alcohol) and poly(vinyl acetate), can be used in the formulations.

It is possible to use colorants such as inorganic pigments, for examples, iron oxide, titanium oxide and Prussian Blue, and organic dye stuffs and metalphthalocyanine dye stuffs and trace nutrients such as salts of iron, manganese, boron, copper, cobalt, molybdenum and zinc.

The active compounds according to the invention can be present in formulations of the types that are commercially available and in use forms, prepared from these formulations, as a mixture with other active compounds, such as baits, sterilizing agents, acaricides, nematicides, fungicides, growth-regulating substances, other insecticides or herbicides. The insecticides include, for example, phosphates, carbamates, carboxylates, chlorinated hydrocarbons, phenylureas and substances produced by microorganisms.

The compounds of this invention may also be present in a pure form and may be mixed with other agents in a tank (tank mix) immediately before use. The compounds of this invention further may be present in a mix with other active compounds (package mix).

The compounds are employed in a customary manner appropriate for the use forms.

The invention also provides an insecticidal composition comprising an insecticidally effective amount of the compounds of the invention and one or more suitable carriers. Suitable carriers that may be used include those such as are described in U.S. Pat. No. 3,996,367 entitled "N,N-Dimethyl-O-[1-Methyl-3-N-Methylcarbaminyl-methyl-pyrazol(5) yl]-Carbamic Acid Ester" issued on Dec. 7, 1976 and assigned to Bayer Aktiengesellschaft.

The invention further provides a method of combating insects which comprises applying to the insects or to a habitat thereof an insecticidally effective amount of a compound according to the invention. An insecticidally effective amount is typically 1 ppm (10% acetone and surfactant).

The invention also provides a fungicidal composition comprising a fungicidally effective amount of the compounds of the invention and one or more suitable carriers. Suitable carriers including those described in U.S. Pat. No. 4,556,661 entitled "Pyridine Derivatives" issued on Dec. 3, 1985 and assigned to Hoffmann-LaRoche, Inc.

These fungicidal compositions contain, as the inert carrier material, at least one of the following ingredients: solid carrier materials; solvents or dispersion media; surface active agents, for example, wetting and emulsifying agents; dispersing agents; and stabilizers. Examples of each of these ingredients may also be found in U.S. Pat. No. 4,556,661, id.

The fungicidal compositions of the invention generally contain between 0.0001 percent by weight and 95 percent by weight of compound or compounds of the invention as active ingredients.

The fungicidal compositions of the present invention can be in forms suitable for storage or shipment. In such forms (e.g., emulsifiable concentrates), the concentration of active ingredients is normally at the higher end of the above concentration range. These forms can then be diluted with the same or different carrier materials to afford active ingredient concentrations suitable for practical use, and such concentrations normally are at the lower end of the above-noted concentration range. Emulsifiable concentrates generally contain from about 5 percent by weight to about 95 percent by weight, preferably from 25 percent by weight to 75 percent by weight, of the compound or compounds of the invention.

The application forms prepared from the above-indicated compositions include ready-for-use solutions, emulsions, foams, suspensions, powders, pastes, soluble powders, dusting agents and granulates.

The concentration of active ingredient in the ready-for-use preparations can vary over wide limits. In spray liquors, the concentration can be, for example, between 0.0001 percent by weight and 20 percent by weight.

The active ingredients can also be used with good effect in the Ultra-Low-Volume process (ULV) where it is possible to formulate spray liquors having preferably from about 0.5 to about 20 percent by weight of active ingredient.

The active ingredients can also be used with good effect in the Low-Volume process and in the High-Volume process where it is possible to formulate spray liquors having from 0.02 to 1.0 and 0.002 to 0.1 percent by weight of active ingredient respectively.

The invention further provides a method of combating fungus which comprises applying to the fungus or to a habitat thereof a fungicidally effective amount of a compound according to the invention. The compounds of the invention are particularly active against wheat leaf rust.

EXAMPLE 1

Preparation of 4,4-dimethyl-3-(N,N-dimethylcarbamoyloxy)-1-phenyl-2-pyrazoline To a solution of 4,4-dimethyl-1-phenyl-3-pyrazolidinone (1.90 g) in a mixture of 25 mL pyridine and 4 mL triethylamine at 0° C. is added N,N-dimethylcarbamoyl chloride (1.37 mL). The reaction mixture is stirred at room temperature for 16 hours. The reaction mixture is diluted with methylene chloride (100 mL) and washed with 10% aqueous hydrochloric acid (200 mL). The organic layer is dried (MgSO$_4$), filtered and evaporated. Chromatography on silica gel gave a light yellow solid. Recrystallization from ethanol gave 1.80 g (73%) of pale yellow crystals. (MP-99°–100° C.; Analysis: C-64.26%, H-7.19%, N-16.04%; H$^1$NMR-$\delta$ 7.6-2H,t; $\delta$ 7.35-2H,d; $\delta$ 7.15-2H,t; $\delta$ 4.1-2H,s; $\delta$ 3.4-3H,s; $\delta$ 3.3-3H,s; $\delta$ 1.7-6H,s).

EXAMPLE 2

The aphicidal activity of the compounds of the present invention is exemplified by the following tests in which insects and mites are continuously maintained in the laboratory on natural or artificial diets. Five insects and one mite species are used for evaluating potential insecticide/acaricide activity. Refer to Table I for specific protocol of each test.

Host plants are grown in 10 ounce styrofoam cups. Plants are grown to the appropriate size for foliar treatment.

Ten mL of the test solution containing 500 ppm active ingredient (AI) is applied per potted plant. The test solution generally consists of 10% acetone in water and 100 ppm Triton X-100 surfactant (sold by Rohn and Haas Co.).

The test consists of:
A. Untreated control;
B. Test compound; and
C. Standard

Two replicates of 10 insects each per test. Test compounds are applied at 20 psi using a hand-held spray gun. The plants are rotated on a turntable during application to assure even coverage. Following spraying, the foliage is air dried.

A. *Aphis fabae*—Treated plants are clipped and a small bouquet of nasturtium is transferred to a testing cage. Insects are released into each cage. A leaf infested with aphids is propped on the test plant. As the leaf dries the aphids move onto the test plant.

B. *Spodoptera exiqua*—Ten second-instar larvae are exposed to treated cotton leaves held in a parafilm-sealed petri dish.

C. *Heliothis veriscens*—Since *H. viresens* is cannibalistic, larvae are isolated in one ounce cups. Two cotton cotyledons are placed in one cup.

D. *Blatella germanica*—Cockroaches of varying ages are anaesthetized with CO$_2$ and removed from the rearing cages. They are then placed onto pretreated filter paper. The filter paper was previously dipped into a 500 ppm solution of the test compound and air dried. A small amount of dry dog food is placed into each dish. The petri dish is covered and sealed with parafilm.

E. *Diabrotica undecimpuntata*—Germinating corn seed is placed onto a moist glass filter paper held in a petri dish bottom. The unit is sprayed with the test compound using a Potter's Spray Tower. Ten larvae are placed in each dish. The dish is then covered and sealed with parafilm.

F. *Tetranychus urticae*—Cotton plants are grown in 1 ounce styrofoam cups. The plants are sprayed with the test compound and then air dried. A mite-infested bean leaf is placed onto the cotton plants and as it dries the mites migrate onto the cotton.

Mortality is assessed after 48 hours exposure. The percent of the control is calculated as:

$$\% \text{ Control} = 100 \times \frac{\text{No. of insects that died}}{\text{No. of insects treated}}$$

The calculated % control is then ranked as follows:

| % Control | Ranking |
| --- | --- |
| 0–9 | 0 |
| 10–29 | 1 |
| 30–49 | 2 |
| 50–79 | 3 |
| 80–100 | 4 |

Evaluation of Test Compounds for Control of Foliar Pathogens

1. Host plants are grown in 13.3×13.3. cm units (Com-Packs®), held in standard greenhouse flats (52×26×6 cm). The soil used is steam-sterilized sandy loam. Plants are grown to the appropriate stage and then treated with the test chemical.

2. Ten mL of the test solution containing 500 ppm AI is applied per unit sample. The appropriate amounts of chemical per unit is calculated as follows:

$$\frac{0.5 \times 10}{100} = \text{Amount of chemical per unit}$$

where;
0.05=500 ppm converted to percent,
10=mL of diluent, and
100=percent AI (active ingredient) of chemical sample, in this case it is 100% or technical grade.

3. A solution of octylphenoxy polyethoxy ethanol (Triton X-100) in acetone (1000 ppm w/w) is used to dissolve the material under test. The solution is diluted with distilled water 1:9 v/v to obtain a final mixture of 10% acetone and 100 ppm of Triton X-100 in water. Further dilution of this stock solution, as required in rate studies, is done by using a diluent consisting of 100 ppm Triton X-100 in water so that a constant concentration of the surfactant is maintained at all levels.

4. The test consists of:
A. Untreated control
B. Test
C. Standard

5. The standards (Table I) are applied at the given rate. Some lesions may occur at these rates.

6. Two replicates per test.

7. Test compounds are applied at 20 psi using a hand-held spray gun. The plants are rotated on a turn table during application to assure even coverage.

8. Following spraying the foliage is air dried.

9. Bean plants are then placed adjacent to mildew-infested beans. After 24 hours exposure the plants are moved to the opposite end of the greenhouse and held until mildew first appears on the control. The test compound is then evaluated. the plants are further held until 100% leaf infection occurs in the control, and a final readout is taken.

10. The remaining test plants: wheat is inoculated with the respective pathogen. Spores are obtained from culture plates and diluted in 1% glucose plus 1 drop of polyethyleneoxide sorbitan monolaurate sold by ICI(-Tween) 20 per 100 mL of solution. Spores are sprayed over the plant foliage at 10 psi using a Devilbiss® spray atomizer. Fifteen mL of spray is applied per greenhouse flat (i.e. 8 units).

11. Following inoculation the plants are placed into an incubation chamber for 48 hours. They are held at 25° C. and 100% RH. The humidity is maintained by an overhead sprayer which produces fine mist for 15 seconds every 15 minutes.

12. Following incubation the plants are placed on a greenhouse bench. An overhead misting unit continues to wet the foliage for 15 seconds every 15 minutes.

13. The activity of the test compound is then evaluated when lesions first appear in the control; generally in 2 to 3 days. The plants are then held until 100% leaf infection occurs in the control, and a final readout is taken.

14. The following information is recorded:

A. Number of healthy plants
B. Number of diseased plants
C. Number of lesions
D. Phytotoxicity, i.e., chlorosis, marginal leaf burning, stunting, unusual growth patterns, etc.

15. The percentage disease control is calculated according to the following formula:

$$MPDC = \frac{MDIC - MDIT}{MDIC} \times 100$$

where;

MPDC = mean percentage of disease control.
MDIC = mean percentage of disease incidence in the untreated control, and
MDIT = mean percentage of disease incidence in treatment.

16. Based on the percentage of disease control, treatments are ranked 0 to 4 using the following scale:

| % Control | Ranking |
| --- | --- |
| 0–9 | 0 |
| 10–29 | 1 |
| 30–49 | 2 |
| 50–79 | 3 |
| 80–100 | 4 |

17. Compounds which facilitate 50% or better control (ranking of 3 or 4) are recommended for secondary screening.

The fungicidal activity of the compounds of the present invention is exemplified by the results in Table II test in which certain compounds of the invention were evaluated for their activity against wheat leaf rust.

TABLE I

Arthropod, Host, and Methods Used for Evaluating Insecticides/Acaricides

| Arthropod | Common Name | Rearing Host | Test Host | Test Stage | Appl. Method | Cage | Standard | Rate (ppm AI) |
| --- | --- | --- | --- | --- | --- | --- | --- | --- |
| Aphis fabae | Bean aphid | Nasturtium | Nasturtium | variable | leaf sprayed | See FIG. 1 | Permethrin (94.8%) | 200 |
| Spodoptera exiqua | Beet armyworm | Artificial diet | Cotton | 2nd instar | leaf sprayed | petri dish | Nudrin 1.8 (methomyl) | 100 |
| Heliothis virescens | Tobacco budworm | Artificial diet | Cotton | 2nd instar | leaf sprayed | 1 oz. cup | Nudrin 1.8 (methomyl) | 100 |
| Blattella germanica | German cockroach | Dog food | Dog food | variable | dipped filter paper | petri dish | Permethrin (94.8%) | 50 |
| Diabrotica undecimpunctata | Corn rootworm | Corn roots | Corn roots | 2nd instar | sprayed roots & filter paper | petri dish | Furadan 4F (carbofuran) | 100 |
| Tetranychus urticae | Spider mite | Beans | Cotton | variable | leaf sprayed | 10 oz. cup | Comite 73% (propargite) | 800 |
| Musca domestica | House Fly | | | | Direct Spray | 2.5 × 9 cm aluminum screen | Permethrin (38.4% ai.) | 100 |

TABLE II

Test Results $$\text{Structure with } R_1, R_2 \text{ on carbamate N; } R_3, R_4 \text{ on carbon; } R_5 \text{ on ring N}$$

| EXAMPLE | R¹ | R² | R³ | R⁴ | R⁵ | Aphid | Fly | Rust |
|---|---|---|---|---|---|---|---|---|
| 1 | Me | Me | Me | Me | Ph | 4 | 4 | 0 |
| 2 | Et | Et | Me | CH₂OH | " | 3 | 0 | 0 |
| 3 | —CH₂CH₂OCH₂CH₂— | | " | " | " | 4 | 0 | 1 |
| 4 | Me | Me | " | " | " | 4 | 0 | 0 |
| 5 | i-Pr | i-Pr | " | " | " | 0 | 0 | 0 |
| 6 | Me | Me | " | " | 4-MePh | 4 | 0 | 2 |
| 7 | —CH₂CH₂OCH₂CH₂— | | " | " | " | 3 | 0 | 2 |
| 8 | Me | Me | " | " | 4-MePh | 4 | 0 | 3 |
| 9 | " | " | H | H | Ph | 4 | 4 | 0 |
| 10 | " | Ph | " | " | 4-OMePh | 1 | 3 | 4 |
| 11 | Me | Me | H | H | 4-MePh | 0 | 1 | 3 |
| 12 | " | " | Me | Me | 4-MePh | 4 | 2 | 0 |
| 13 | " | " | " | Me₂NCOOCH₂ | Ph | 2 | 0 | 0 |
| 14 | " | " | " | " | 4-MePh | 4 | 3 | 0 |
| 15 | " | " | " | " | 4-OMePh | 1 | 2 | 0 |
| 16 | Me | Me | Me | Me | —CH₂CH=CH₂ | 4 | — | — |
| 17 | Me | Me | Me | Me | —CH₂—Ph | 4 | — | — |
| 18 | Me | Me | Me | Me | —CH₂—C₆H₄—CH₃ | 4 | — | — |
| 19 | Me | Me | Me | Me | —CH₂—C₆H₄—F | 4 | — | — |
| 20 | Me | Me | Me | Me | —CH₂—C₆H₄—C(CH₃)₃ | 4 | — | — |
| 21 | Me | Me | Me | Me | —C₆H₄—NO₂ | 4 | — | — |
| 22 | Me | Me | Me | 2-hydroxy-isopropyl | 4-MePh | 4 | 0 | 0 |
| 23 | Me | Me | Me | Me | 2-BrPh | 4 | 0 | 0 |
| 24 | Me | Me | Me | Me | 4-BrPh | 4 | 3 | 2 |
| 25 | Me | Me | Me | Me | 2-MePh | 4 | 1 | 0 |
| 26 | Me | Me | Me | n-Bu | 4-MePh | 4 | 0 | 0 |
| 27 | Me | Me | Me | isobutoxymethyl | 4-MePh | 4 | 3 | 0 |
| 28 | Me | Me | Me | Me | 4-n-BuPh | 4 | 4 | 0 |
| 29 | Me | Me | Me | BrCH₂ | Ph | 4 | 0 | 0 |
| 30 | Me | Me | Me | HO(CH₂)₂ | Ph | 4 | 0 | 0 |
| 31 | Me | Me | Me | Me | 4-(N,N-dimethylcarbamoyloxy-carbonylphenyl | 4 | 0 | 0 |
| 32 | Me | Me | Me | Me | 4-[N-(N,N-dimethylcarbamoyl)-methanesulfonamido]-phenyl | 4 | 0 | 0 |

TABLE II-continued

Test Results

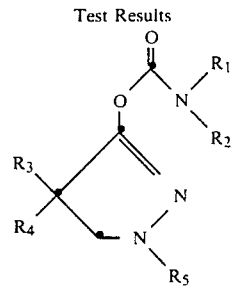

| EXAMPLE | R¹ | R² | R³ | R⁴ | R⁵ | Aphid | Fly | Rust |
|---|---|---|---|---|---|---|---|---|
| 33 | Me | Me | Me | Me | 2-FPh | 4 | 3 | 0 |
| 34 | Me | Me | Me | Me | 4-SO₂MePh | 4 | 4 | 0 |
| 35 | Me | Me | Me | Me | 3-FPh | 3 | 3 | 0 |
| 36 | Me | Me | Me | Me | 4-FPh | 3 | 3 | 0 |
| 37 | Me | Me | Me | Me | 2,4,6-Cl₃Ph | 4 | 1 | 0 |
| 38 | Me | Me | Me | Me | 3,4-Cl₂Ph | 4 | 2 | 0 |
| 39 | Me | Me | Me | Me | 4-ClPh | 4 | 3 | 0 |

As can be seen from the above results, particularly preferred compounds include compounds wherein $R^1$ is ethyl, methyl or isopropyl, $R^2$ is ethyl, methyl, isopropyl or phenyl, $R^1$ and $R^2$ together is oxydiethylene, $R^3$ is hydrogen and methyl and $R^4$ is hydroxy, isobutoxymethyl, n-butyl, 2-hydroxyisopropyl, bromomethyl, 2-hydroxyethyl and hydrogen, and $R^5$ is phenyl, benzyl, allyl, methylbenzyl, fluorobenzyl, tertiary butylbenzyl, nitrophenyl, bromophenyl, n-butylphenyl, 4-(N,N-dimethylcarbamoyloxycarbonylphenyl, fluorophenyl, 4-[N-(N,N-dimethylcarbamoyl)methanesulfonamido]-phenyl, methylsulfonylphenyl, 2,4,6-trichlorophenyl, 3,4-dichlorophenyl, tolyl and chlorophenyl.

Thus, preferred compounds of the invention for insecticidal use include:

4,4-dimethyl-3-(N,N-dimethylcarbamoyloxy)-1-phenyl-2-pyrazoline,
3-(N,N-diethylcarbamoyloxy)-4-hydroxymethyl-4-methyl-1-phenyl-2-pyrazoline,
4-hydroxymethyl-4-methyl-3-morpholinocarbonyloxy-1-phenyl-2-pyrazoline,
3-(N,N-dimethylcarbamoyloxy)-4-hydroxymethyl-4-methyl-1-phenyl-2-pyrazoline,
3-(N,N-dimethylcarbamoloxy)-4-hydroxymethyl-4-methyl-1-(4-tolyl)-2-pyrazoline,
4-hydroxymethyl-4-methyl-1-(4-tolyl)-3-morpholinocarbonyloxy-2-pyrazoline,
3-(N,N-dimethylcarbamoyloxy)-4-hydroxymethyl-4-methyl-1-(4-tolyl)-2-pyrazoline,
3-(N,N-dimethylcarbamoyloxy)-1-phenyl-2-pyrazoline,
1-methoxyphenyl-3-(N-methyl-N-phenylcarbamoyloxy-2-pyrazoline,
1-methoxyphenyl-4,4-dimethyl-3-(N,N-dimethylcarbamoyloxy)-2-pyrazoline,
4-(N,N-dimethylcarbamoyloxymethyl)-3-(N,N-dimethylcarbamoyloxy)-4-methyl-1-(4-tolyl)-2-pyrazoline,
1-allyl-4,4-dimethyl-3-(N,N-dimethylcarbamoyloxy)-2-pyrazoline,
1-benzyl-4,4-dimethyl-3-(N,N-dimethylcarbamoyloxy)-2-pyrazoline,
4,4-dimethyl-1-(2-methylbenzyl)-3-(N,N-dimethylcarbamoyloxy)-2-pyrazoline,
1-(4-fluorobenzyl-4,4-dimethyl-3-(N,N-dimethylcarbamoyloxy)-2-pyrazoline,
1-(4-t-butyl)-4,4-dimethyl-3-(N,N-dimethylcarbamoyloxy)-2-pyrazoline,
4,4-dimethyl-1-(4-nitrophenyl)-3-(N,N-dimethylcarbamoyloxy)-2-pyrazoline,
4-(2-hydroxyisopropyl)-3-(N,N-dimethylcarbamoyloxy)-4-methyl-1-(4-tolyl)-2-pyrazoline,
1-(2-bromophenyl)-4,4-dimethyl-3-(N,N-dimethylcarbamoyloxy)-2-pyrazoline,
1-(4-bromophenyl)-4,4-dimethyl-3-(N,N-dimethylcarbamoyloxy)-2-pyrazoline,
4,4-dimethyl-3-(N,N-dimethylcarbamoyloxy)-1-(2-tolyl)-2-pyrazoline.
4-n-butyl-3-(N,N-dimethylcarbamoyloxy)-4-methyl-1-(4-tolyl)-2-pyrazoline,
3-(N,N-dimethylcarbamoyloxy)-4-(isobutoxymethyl)-4-methyl-1-(4-(tolyl)-2-pyrazoline,
1-(4-n-butylphenyl)-4,4-dimethyl-3-(N,N-dimethylcarbamoyloxy)-2-pyrazoline,
4-bromomethyl-3-(N,N-dimethylcarbamoyloxy)-4-methyl-1-phenyl-2-pyrazoline,
4-(2-hydroxyethyl)-3-(N,N-dimethylcarbamoyloxy)-4-methyl-1-phenyl-2-pyrazoline,
4,4-dimethyl-3-(N,N-dimethylcarbamoyloxy)-1-[4-(N,N-dimethylcarbamoyloxycarbonyl)phenyl]-2-pyrazoline,
4,4-dimethyl-1-{4-[N-(N,N-dimethylcarbamoyl)methanesulfonamido]phenyl}-2-pyrazoline,
1-(2-fluorophenyl)-4,4-dimethyl-3-(N,N-dimethylcarbamoyloxy)-2-pyrazoline,
4,4-dimethyl-3-(N,N-dimethylcarbamoyloxy)-1-(4-methylsulfonylphenyl)-2-pyrazoline,
4,4-dimethyl-3-(N,N-dimethylcarbamoyloxy)-1-(2,4,6-trichlorophenyl-2-pyrazoline,
1-(3,4-dichlorophenyl)-4,4-dimethyl-3-(N,N-dimethylcarbamoyloxy)-2-pyrazoline,carbamoyloxy)-2-pyrazoline,
1-(4-chlorophenyl)-4,4-dimethyl-3-(N,N-dimethylcarbamoyloxy)-2-pyrazoline,
4,4-dimethyl-1-(3-fluorophenyl)-3-(N,N-dimethylcarbamoyloxy)-2-pyrazoline,
4,4-dimethyl-1-(4-fluorophenyl)-3-(N,N-dimethylcarbamoyloxy)-2-pyrazoline.

More particularly preferred compounds of the invention for insecticidal use include:

1-allyl-4,4-dimethyl-3-(N,N-dimethylcarbamoyloxy)-2-pyrazoline, 4,4-dimethyl-1-(4-nitrophenyl)-3-(N,N-dimethylcarbamoyloxy)-2-pyrazoline.

4,4-dimethyl-1-(4-nitrophenyl)-3-(N,N-dimethylcarbamoyloxy)-2-pyrazoline, 1-(2-bromophenyl)-4,4-dimethyl-3-(N,N-dimethylcarbamoyloxy)-2-pyrazoline, 4,4-dimethyl-3-(N,N-dimethylcarbamoyloxy)-1-[4-(N,N-dimethylcarbamoyloxycarbonyl)phenyl]-2-pyrazoline and 4,4-dimethyl-3-(N,N-dimethylcarbamoyloxy)-1-(4-methylsulfonylphenyl)-2-pyrazoline.

Preferred compounds for fungicidal use include:

4-hydroxymethyl-4-methyl-1-(4-tolyl)-3-morpholinocarbonyloxy-2-pyrazoline,
1-(4-methoxyphenyl)-3-(N-methyl-N-phenylcarbamoyloxy)-2-pyrazoline,
3-(N,N-dimethylcarbamoyloxy)-1-(4-methoxyphenyl)-2-pyrazoline
1-(4-bromophenyl)-4,4-dimethyl-3-(N,N-dimethylcarbamoyloxy)-2-pyrazoline.

The invention has been described in detail with particular reference to preferred embodiments thereof, but it will be understood that variations and modifications can be effected within the spirit and scope of the invention.

What is claimed is:

1. A compound having the structure:

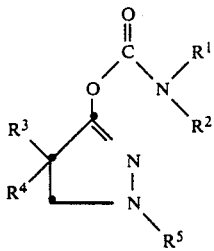

wherein:
$R^1$ and $R^2$ are selected independently from a group consisting of hydrogen, with the proviso that only one of $R^1$ and $R^2$ can be hydrogen and alkyl of from 1-20 carbon atoms;
$R^3$ and $R^4$ are selected independently from a group consisting of hydrogen and alkyl of from 1-20 carbon atoms;
$R^5$ is selected from a group consisting of alkyl of 1-10 carbon atoms, alkenyl of 1-10 carbon atoms and substituted or unsubstituted aryl of 6-20 carbon atoms wherein the substituents are selected from alkyl, halogen, nitro and methylsulfonyl.

2. The compound of claim 1 wherein $R^1$ is ethyl, methyl or isopropyl.

3. The compound of claim 1 wherein $R^2$ is ethyl, methyl, or isopropyl.

4. The compound of claim 1 wherein $R^3$ is hydrogen or methyl.

5. The compound of claim 1 wherein $R^4$ is methyl, hydrogen, or n-butyl

6. The compound of claim 1 wherein $R^5$ is phenyl, allyl, nitrophenyl, bromophenyl, n-butylphenyl, fluorophenyl, methylsulfonylphenyl, 2,4,6-trichlorophenyl,3,4-dichlorophenyl, tolyl and chlorophenyl.

7. A compound having the structure:

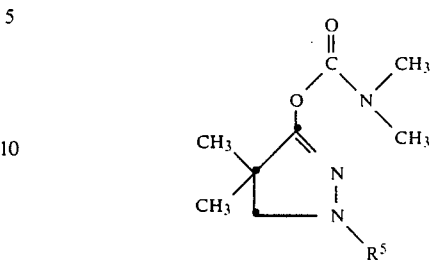

wherein:
$R^5$ is selected from a group consisting of alkyl of 1-10 carbon atoms, alkenyl of 1-10 carbon atoms and substituted and unsubstituted aryl of 6-20 nuclear carbon atoms wherein the substituents are selected from alkyl, halogen, nitro and methylsulfonyl.

8. A compound according to claim 7 wherein $R^5$ is independently selected from a group consisting of phenyl, allyl, nitrophenyl, bromophenyl, n-butylphenyl, fluorophenyl, methylsulfonylphenyl, 2,4,6-trichlorophenyl,3,4-dichlorophenyl, tolyl and chlorophenyl.

9. An insecticidal composition comprising an insecticidally effective amount of a compound according to claim 1 and one or more suitable carriers.

10. Insecticidal compositions according to claim 9 comprising:
4,4-dimethyl-3-(N,N-dimethylcarbamoyloxy)-1-phenyl-2-pyrazoline,
3-(N,N-dimethylcarbamoyloxy)-1-phenyl-2-pyrazoline,
1-allyl-4,4-dimethyl-3-(N,N-dimethylcarbamoyloxy)-2-pyrazoline,
1-(4-t-butyl)-4,4-dimethyl-3-(N,N-dimethylcarbamoyloxy)-2-pyrazoline,
4,4-dimethyl-1-(4-nitrophenyl)-3-(N,N-dimethylcarbamoyloxy)-2-pyrazoline,
1-(2-bromophenyl-4,4-dimethyl-3-(N,N-dimethylcarbamoyloxy)-2-pyrazoline,
1-(4-bromophenyl)-4,4-dimethyl-3-(N,N-dimethylcarbamoyloxy)-2-pyrazoline,
4,4-dimethyl-3-(N,N-dimethylcarbamoyloxy)-1-(2-tolyl)-2-pyrazoline,
4-n-butyl-3-(N,N-dimethylcarbamoyloxy)-4-methyl-1-(4-tolyl)-2-pyrazoline,
1-(2-fluorophenyl)-4,4-dimethyl-3-(N,N-dimethylcarbamoyloxy)-2-pyrazoline,
4,4-dimethyl-3-(N,N-dimethylcarbamoyloxy)-1-(4-methylsulfonylphenyl)-2-pyrazoline,
4,4-dimethyl-3-(N,N-dimethylcarbamoyloxy)-1-(2,4,6-trichlorophenyl-2-pyrazoline,
1-(3,4-dichlorophenyl)-4,4-dimethyl-3-(N,N-dimethylcarbamoyloxy)-2-pyrazoline and
1-(4-chlorophenyl)-4,4-dimethyl-3-(N,N-dimethylcarbamoyloxy)-2-pyrazoline.

11. Insecticidal compositions according to claim 9 comprising:
1-allyl-4,4-dimethyl-3-(N,N-dimethylcarbamoyloxy)-2-pyrazoline,
4,4-dimethyl-1-(4-nitrophenyl)-3-(N,N-dimethylcarbamoyloxy)-2-pyrazoline,
1-(2-bromophenyl-4,4-dimethyl-3-(N,N-dimethylcarbamoyloxy)-2-pyrazoline, and
4,4-dimethyl-3-(N,N-dimethylcarbamoyloxy)-1-(4-methylsulfonylphenyl)-2-pyrazoline.

12. Insecticidal compositions according to claim 9 comprising:
4,4-dimethyl-3-(N,N-dimethylcarbamoyloxy)-1-phenyl-2-pyrazoline,
3-(N,N-dimethylcarbamoyloxy)-1-phenyl-2-pyrazoline,
1-(4-bromophenyl)-4,4-dimethyl-3-(N,N-dimethylcarbamoyloxy)-2-pyrazoline,
1-(4-n-butylphenyl)-4,4-dimethyl-3-(N,N-dimethylcarbamoyloxy-2-pyrazoline,
1-(2-fluorophenyl)-4,4-dimethyl-3-(N,N-dimethylcarbamoyloxy)-2-pyrazoline,
4,4-dimethyl-3-(N,N-dimethylcarbamoyloxy)-1-(4-methylsulfonylphenyl)-2-pyrazoline,
4,4-dimethyl-1-(3-fluorophenyl)-3-(N,N-dimethylcarbamoyloxy)-2-pyrazoline,
4,4-dimethyl-1-(4-fluorophenyl)-3-(N,N-dimethylcarbamoyloxy)-2-pyrazoline,
1-(4-chlorophenyl)-4,4-dimethyl-3-(N,N-dimethylcarbamoyloxy)-2-pyrazoline.

13. A method of combating insects which comprises applying to the insects or to a habitat thereof an insecticidally effective amount of a compound according to claim 1.

14. A method of combating insects which comprises applying to the insects or to a habitat thereof an insecticidally effective amount of a compound according to claim 7.

15. A fungicidal composition comprising a fungicidally effective amount of a compound according to claim 1 and one or more suitable carriers.

16. A fungicidal composition according to claim 15 comprising:
1-(4-bromophenyl)-4,4-dimethyl-3-(N,N-dimethylcarbamoyloxy)-2-pyrazoline.

17. A method of combating fungus which comprises applying to the fungus or to a habitat thereof a fungicidally effective amount of a compound having the structure

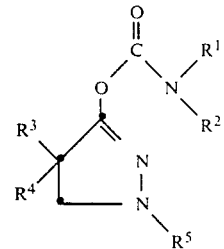

wherein:
$R^1$ and $R^2$ are selected independently from a group consisting of hydrogen, with the proviso that only one of $R^1$ and $R^2$ can be hydrogen and alkyl of from 1-20 carbon atoms;
$R^3$ and $R^4$ are selected independently from a group consisting of hydrogen and alkyl of from 1-20 carbon atoms;
$R^5$ is selected from a group consisting of alkyl of 1-10 carbon atoms, alkenyl of 1-10 carbon atoms and substituted or unsubstituted aryl of 6-20 carbon atoms wherein the substituents are selected from alkyl, halogen, nitro and methylsulfonyl.

18. A method of combating fungus which comprises applying to the fungus or to a habitat thereof a fungicidally effective amount of a compound according to claim 7.

19. A method according to claim 17, wherein the fungus is wheat leaf rust.

* * * * *